(12) United States Patent
Wang et al.

(10) Patent No.: US 11,180,530 B2
(45) Date of Patent: *Nov. 23, 2021

(54) SALT OF PHENYLPROPIONAMIDE DERIVATIVE AND PREPARATION METHOD THEREFOR

(71) Applicants: Jiangsu Hengrui Medicine CO., LTD., Jiangsu (CN); Shanghai Hengrui Pharmaceutical CO., LTD, Shanghai (CN)

(72) Inventors: Lin Wang, Shanghai (CN); Jingquan Ye, Shanghai (CN); Qiyun Shao, Shanghai (CN); Jun Feng, Shanghai (CN); Feng He, Shanghai (CN); Xiaoli Cao, Jiangsu (CN); Yahui Ma, Jiangsu (CN)

(73) Assignees: Jiangsu Hengrui Medicine CO., LTD., Jiangsu (CN); Shanghai Hengrui Pharmaceutical CO., LTD, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/769,764

(22) PCT Filed: Dec. 5, 2018

(86) PCT No.: PCT/CN2018/119309
§ 371 (c)(1),
(2) Date: Jun. 4, 2020

(87) PCT Pub. No.: WO2019/109934
PCT Pub. Date: Jun. 13, 2019

(65) Prior Publication Data
US 2020/0331963 A1   Oct. 22, 2020

(30) Foreign Application Priority Data
Dec. 6, 2017  (CN) .......................... 201711272474.1

(51) Int. Cl.
*A61K 38/07* (2006.01)
*C07K 1/06* (2006.01)
*C07K 5/11* (2006.01)
*A61P 23/00* (2006.01)
*A61P 29/00* (2006.01)

(52) U.S. Cl.
CPC ............ *C07K 5/1019* (2013.01); *A61P 23/00* (2018.01)

(58) Field of Classification Search
CPC .......... A61K 38/07; A61P 23/00; A61P 29/00; C07K 1/06; C07K 5/1019; C07K 5/11; C07D 295/18
See application file for complete search history.

(56) References Cited

U.S. PATENT DOCUMENTS

| | | | |
|---|---|---|---|
| 8,809,278 B2 | 8/2014 | Aldrich et al. | |
| 10,035,767 B2* | 7/2018 | Murayama | C07K 1/128 |
| 2016/0250277 A1 | 9/2016 | Chalmers et al. | |
| 2019/0144499 A1* | 5/2019 | Li | C07K 5/1008 |
| | | | 514/15.4 |

FOREIGN PATENT DOCUMENTS

| | | |
|---|---|---|
| CN | 104271552 A | 1/2015 |
| CN | 108290926 A | 7/2018 |
| WO | 9932510 A1 | 7/1999 |
| WO | 20071398 A2 | 1/2007 |
| WO | 2008060552 A2 | 5/2008 |
| WO | 2013184794 A2 | 12/2013 |
| WO | 2014089019 A1 | 6/2014 |
| WO | 2014184356 A1 | 11/2014 |
| WO | 2015065867 A2 | 5/2015 |
| WO | 2017211272 A1 | 12/2017 |

OTHER PUBLICATIONS

Kiviranta et al. "N-(3-(4-Hydroxyphenyl)-propenoyl)-amino acid tryptamides as SIRT2 inhibitors" Bioorganic Medicinal Chemistry Letters, 2007, 7(9), 2448-2451.

Holvey et al. "Selective Targeting of the TPX2 Site of Importin-a Using Fragment-Based Ligand Design" ChemMedChem, 2015, 10 (7), 1232-1239.

Czekelius et al. "Catalytic Enantioselective Conjugate Reduction of ?, ?-Disubstituted Nitroalkenes" Angewandte chemie, international edition, 2003,42 (39), 4793-4795.

Nakao et al. "CJ-023,423, a Novel, Potent and Selective Prostaglandin KOR Receptor Antagonist with Anti-hyperalgesic Properties". The Journal of Pharmacology and Experimental Therapeutics, 2007, 322(2)1686-694.

Feb. 26, 2019 (WO) International Search Report PCT/CN2018/119309.

* cited by examiner

*Primary Examiner* — Julie Ha
(74) *Attorney, Agent, or Firm* — Banner & Witcoff, Ltd.

(57) ABSTRACT

A salt of a phenylpropionamide derivative and a preparation method therefor is described. Specifically, the salt of the compound of formula (I) has good stability, and can be better used in clinical treatment. The process for preparing the salt of the compound of formula (I) of the present invention is simple and easy to operate.

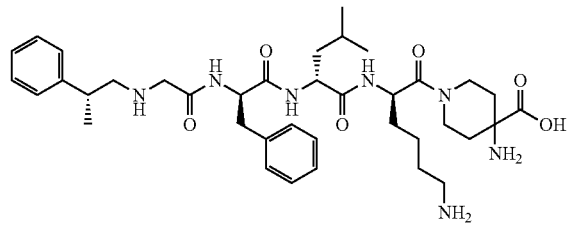

17 Claims, 1 Drawing Sheet

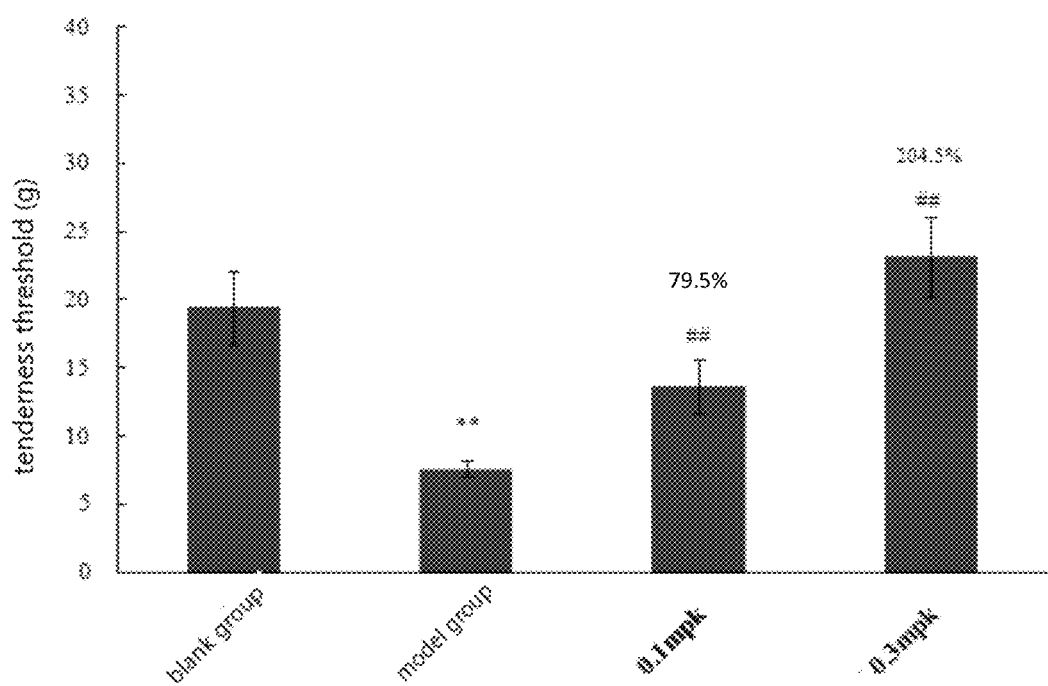

SALT OF PHENYLPROPIONAMIDE DERIVATIVE AND PREPARATION METHOD THEREFOR

RELATED APPLICATION DATA

This application is a National Stage Application under 35 U.S.C. 371 of co-pending PCT application number PCT application no. PCT/CN2018/119309, filed Dec. 5, 2018; which claims the benefit of Chinese Patent Application number CN201711272474.1, filed Dec. 6, 2017, each of which are hereby incorporated by reference in their entireties.

FIELD OF INVENTION

The invention relates to a salt of 4-amino-1-((2R,5R,8R,14R)-2-(4-aminobutyl)-8-benzyl-5-isobutyl-4,7,10-trioxo-14-phenyl-3,6,9,12-tetraazapentadecan-1-acyl)piperidine-4-carboxylic acid, and a preparation method therefor, as well as a use thereof as a κ opioid receptor (KOR receptor) agonist and a use thereof in manufacturing a medicament for treating and/or preventing pain and pain-related diseases.

PRIOR ARTS

Opioid receptor is a kind of important G protein coupled receptor, which is a target for the combination of endogenous opioid peptides and opioid medicines, the activation of opioid receptor have a regulation effect on the nervous systematic immunity and the endocrine system, and opioid medicines are currently the strongest and commonly used central analgesics. Endogenous opioid peptides are naturally generated opioid active substances in mammals, at present, well-known endogenous opioid peptides are roughly divided into enkephalin, endorphin, dynorphin and neoendorphin, and there are corresponding opioid receptors present in the central nervous system, namely μ, δ, κ receptors, etc.

κ-opioid receptor (KOR) consists of 380 amino acids, and dynorphin is its endogenous ligand. It is expressed in sensory neurons, dorsal root ganglion cells and primary afferent neuron terminals, and participates in important physiological activities such as pain sensation, neuroendocrine, emotional behavior and cognition and so on. KOR is also coupled with inward rectifying potassium channel and N-type calcium ion channel. KOR agonist can inhibit (calcium ion dependent) the release of substance P from peripheral sensory nerve endings before injury and inflammation, which may be the reason why KOR agonist has anti-injury and anti-inflammatory effects. In addition to dynorphin, various natural alkaloids and synthetic ligands can also be combined with KOR. KOR provides a natural addiction control mechanism, therefore, medicines as receptor agonists have potential for medicine addiction treatment.

KOR agonist medicines include asimadoline, U-50488 and naloxone, patent applications disclosing KOR agonist include WO20071398, WO2008060552, WO09932510, WO2013184794, WO2014089019, WO2014184356 and WO2015065867.

WO2017211272 (application No. PCT/CN2017/087328, date of application 2017 Jun. 6) discloses a KOR agonist compound, which has obvious agonistic effect on h-KOR receptor, good pharmacokinetic properties, and can improve pain, which has more prominent advantages, the compound thereof has a structure shown by formula (I):

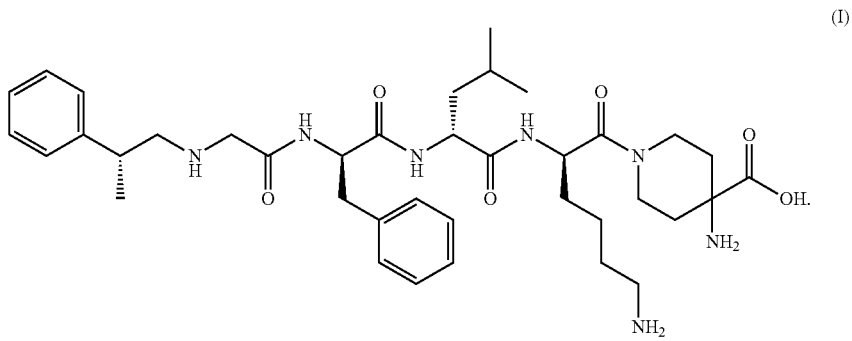 [SMILES: CC(C)C[C@@H](NC(=O)[C@@H](Cc1ccccc1)NC(=O)CNC[C@H](C)c1ccccc1)C(=O)N[C@H](CCCCN)C(=O)N1CCC(N)(C(=O)O)CC1]

As the solubility of the compound represented by formula (I) is low, in order to further improve the solubility of the compound, we have carried out salt formation research on the compound represented by formula (I), and the investigated salts include acetate, hydrochloride, phosphate, citrate, benzoate or fumarate, etc; the solubility of the product is greatly improved after salt formation, and the stability of salt and other issues are also investigated, which has an important research significance in treating pain.

Content of the Present Invention

The technical problem to be solved by the present invention is to provide a salt of 4-amino-1-((2R,5R,8R,14R)-2-(4-aminobutyl)-8-benzyl-5-isobutyl-4,7,10-trioxo-14-phenyl-3,6,9,12-tetraazapentadecan-1-acyl)piperidine-4-carboxylic acid, the salt has good stability and can be better applied to clinic.

The technical solution of the present invention is as follows.

The present invention provides a pharmaceutically acceptable salt of the compound 4-amino-1-((2R,5R,8R,14R)-2-(4-aminobutyl)-8-benzyl-5-isobutyl-4,7,10-trioxo-14-phenyl-3,6,9,12-tetraazapentadecan-1-acyl)piperidine-4-carboxylic acid, as represented by formula (I),

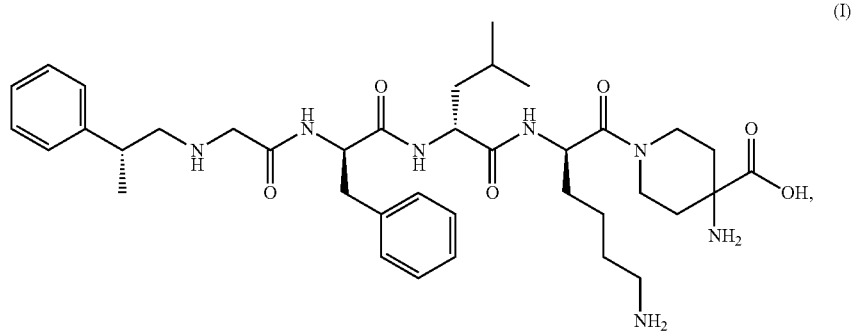 [SMILES: CC(C)C[C@@H](NC(=O)[C@@H](Cc1ccccc1)NC(=O)CNC[C@H](C)c1ccccc1)C(=O)N[C@H](CCCCN)C(=O)N1CCC(N)(C(=O)O)CC1]

(I)

the pharmaceutically acceptable salt is an inorganic salt or an organic salt, preferably acetate, hydrochloride, phosphate, citrate, benzoate or fumarate.

Preferably, the molar ratio of the compound represented by formula (I) to the acid (radical) in the pharmaceutically acceptable salt is 1:1 to 1:5, preferably 1:1, 1:2 or 1:3.

More preferably, the molar ratio of the compound represented by formula (I) to the hydrogen chloride molecules in the pharmaceutically acceptable salt is preferably 1:1, 1:2 or 1:3, more preferably 1:3;

the molar ratio of the compound represented by formula (I) to the phosphoric acid molecules is preferably 1:3;

the molar ratio of the compound represented by formula (I) to the citric acid molecules is preferably 1:1, 1:2 or 1:3, more preferably 1:1;

the molar ratio of the compound represented by formula (I) to the benzoic acid molecules is preferably 1:2;

the molar ratio of the compound represented by formula (I) to fumaric acid molecules is preferably 1:2.

The present invention also provides a method for preparing the pharmaceutically acceptable salt, which comprises a step of salification reaction of the compound represented by formula (I) with a corresponding acid.

In the method, the salification reaction is carried out in a solvent, and the solvent is preferably an alcohol solvent, a halogenated hydrocarbon solvent, an ether solvent, a nitrile solvent, a mixed solvent of an alcohol solvent and an ether solvent or a mixed solvent of a halogenated hydrocarbon solvent and an ether solvent; the alcohol solvent is preferably methanol, ethanol, isopropanol or n-butanol, the ether solvent is preferably diethyl ether, methyl tert-butyl ether, isopropyl ether or dioxane, the nitrile solvent is preferably acetonitrile, and the halogenated hydrocarbon solvent is preferably dichloromethane.

In an alternative embodiment, the mixed solvent of the alcohol solvent and the ether solvent is preferably a mixed solvent of ethanol/isopropyl ether or a mixed solvent of ethanol/isopropyl alcohol/isopropyl ether. In another alternative embodiment, the mixed solvent of the halogenated hydrocarbon solvent and the ether solvent is preferably a mixed solvent of dichloromethane/isopropyl ether.

Preferably, when the salification reaction is completed, the step of adding an antisolvent, volatilizing the solvent or cooling is further included, wherein the antisolvent is preferably an ether solvent, and the ether solvent is preferably diethyl ether, methyl tert-butyl ether, isopropyl ether or dioxane.

The present invention also provides a method for preparing the pharmaceutically acceptable salt, wherein a salt conversion method is employed, preferably, converting trifluoroacetate into acetate. In an alternative embodiment, the salt conversion method comprises the trifluoroacetate of the compound represented by formula (I) is subject to high performance liquid chromatography and eluted with water containing acetic acid as an eluent, concentrating, and drying to obtain the acetate of the compound represented by formula (I).

In the salt conversion method, the eluent may further comprise ammonium acetate, acetonitrile or ammonium acetate/acetonitrile.

Preferably, the volume ratio of the acetic acid in the eluent is 0.1%.

The present invention also provides a pharmaceutical composition comprising the pharmaceutically acceptable salt described above, and optionally a pharmaceutically acceptable carrier, diluent or excipient.

The present invention also provides a use of the salt or the pharmaceutical composition in manufacturing a medicament for preventing and/or treating related diseases mediated by κ opioid receptor agonist; the disease is selected from the group consisting of pain, inflammation, pruritus, edema, hyponatremia, hypokalemia, intestinal obstruction, cough and glaucoma, preferably pain; the pain is preferably selected from the group consisting of neuropathic pain, trunk pain, visceral pain, skin pain, arthritic pain, kidney stone pain, uterine spasm, dysmenorrhea, endometriosis, dyspepsia, post-surgical pain, post-medical treatment pain, eye pain, otitis pain, explosive cancer pain and pain associated with GI disorder.

DETAILED DESCRIPTION OF THE PREFERRED EMBODIMENT

Unless otherwise specified, scientific and technical terms used herein in the description and claims of this application have the meanings commonly understood by those skilled in the art. However, in order to better understand the present invention, definitions and explanations of some relevant terms are provided below. In addition, when the definition and interpretation of terms provided in this application are inconsistent with the meaning commonly understood by those skilled in the art, the definition and interpretation of terms provided in this application shall prevail.

The term "halo" used in the present invention refers to being substituted by "halogen atom", and "halogen atom" refers to fluorine atom, chlorine atom, bromine atom, iodine atom, etc.

The term "$C_{1-6}$ alkyl" used in the present invention represents for a linear or branched alkyl group having 1 to 6 carbon atoms, and specific examples include, but are not limited to, methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, and the like.

The term "ether solvent" used in the present invention represents for a chain compound or a cyclic compound having an ether bond —O— and 1 to 10 carbon atoms, and specific examples include, but are not limited to, tetrahydrofuran, diethyl ether, iso-propyl ether, propylene glycol monomethyl ether, methyl tert-butyl ether or 1,4-dioxane.

The term "alcohol solvent" used in the present invention refers to the solvent derived from substituting one or more than one hydrogen atoms on "$C_{1-6}$ alkyl" with one or more "hydroxyl (—OH)", the "hydroxyl" and "$C_{1-6}$ alkyl" are as defined above, and specific examples include, but are not limited to, methanol, ethanol, iso-propanol, n-propanol, iso-pentanol or trifluoroethanol.

The term "nitrile solvent" used in the present invention refers to the solvent derived from substituting one or more than one hydrogen atoms on "$C_{1-6}$ alkyl" with one or more "cyano (—CN)", the "cyano" and "$C_{1-6}$ alkyl" are as defined above, and specific examples include, but are not limited to, acetonitrile or propionitrile.

The "halogenated hydrocarbon solvent" used in the present invention refers to the solvent derived from substituting one or more than one hydrogen atoms on "$C_{1-6}$ alkyl" with one or more "halogen atoms", the "halogen atom" and "$C_{1-6}$ alkyl" are as defined above, and specific examples include, but are not limited to, methyl chloride, dichloromethane, chloroform or carbon tetrachloride.

The term "mixed solvent" used in the present invention refers to a solvent obtained by mixing one or more than one different kinds of organic solvents in a certain ratio, or a solvent obtained by mixing an organic solvent with water in a certain ratio; the mixed solvent is preferably one or more than one alcohol mixed with one or more than one ether, or one or more than one halogenated hydrocarbon solvent mixed with one or more than one ether solvent; the alcohol solvent, the ether solvent and the halogenated hydrocarbon solvent are as defined above; the certain ratio is 0.05:1-1: 0.05, preferably 1:1, 1:2, 1:3, 1:4, 1:5, 1:8, 1:10 or 1:20.

The present invention also relates to a pharmaceutical preparation comprising the salt of the compound represented by formula (I) and optionally one or more than one pharmaceutical carriers and/or diluents. The pharmaceutical preparation can be made into any pharmaceutically acceptable dosage form. For example, the salt or pharmaceutical preparation of the present invention can be formulated into tablets, capsules, pills, granules, solutions, suspensions, syrups, injections (including injection, sterile powder for injection and concentrated solution for injection), suppositories, inhalants or sprays.

In addition, the pharmaceutical preparation of the present invention can also be applied to patients or subjects in need of such treatment in any suitable mode of administration, such as oral, parenteral, rectal, pulmonary or local administration, etc. When used for oral administration, the pharmaceutical composition can be formulated into oral preparations, such as oral solid preparations, e.g. tablets, capsules, pills, granules and the like; or oral liquid preparation, such as oral solution, oral suspension, syrup, etc. When formed into oral preparation, the pharmaceutical preparation may also contains suitable fillers, binders, disintegrates, lubricants, etc. When used for parenteral administration, the pharmaceutical preparation can be formulated into injection, including injection liquid, sterile powder for injection and concentrated solution for injection. When formed into injections, the pharmaceutical composition can be produced by conventional methods in the prior pharmaceutical field. When formulated into injections, there can be no additives added into the pharmaceutical preparation, whereas appropriate additives can be added according to the nature of the medicament. When used for rectal administration, the pharmaceutical preparation can be formulated into suppository, etc. When used for pulmonary administration, the pharmaceutical preparation can be formulated into inhalant or spray, etc. In certain preferred embodiments, therapeutically and/or prophylactically effective amount of the salt of the present invention is present in the pharmaceutical preparation or medicament. In certain preferred embodiments, the salt of the present invention is present in a unit dose form in a pharmaceutical preparation or medicament.

Advantageous Effects of the Present Invention

Compared with the prior art, the technical solution of the present invention has the following advantages.

Studies show that the salt of the compound represented by formula (I) prepared by the present invention has high purity, small change in HPLC purity and high chemical stability under the conditions of illumination, high temperature and high humidity; the salt of the compound represented by formula (I) obtained by the technical solution of the present invention can meet the medical requirements of production, transportation and storage, has stable production process, can be repeatedly controlled, and can be suitable for industrial production.

BRIEF DESCRIPTION OF DRAWINGS

FIG. 1 effects of the compound represented by formula (I) on carrageenan-induced inflammatory pain in rats.

DETAILED DESCRIPTION OF THE PREFERRED EMBODIMENT

The present invention will be further explained in more detail below with reference to the embodiments, which are only in order to illustrate the technical solution of the present invention and do not limit the essence and scope of the present invention.

Test conditions for apparatus used in the experiments.

The structure of the compound is determined by nuclear magnetic resonance (NMR) or/and mass spectrometry (MS). NMR shift (d) is given in units of $10^{-6}$ (ppm). NMR was determined by Bruker AVANCE-400 NMR instrument, the determination solvent was deuterated dimethyl sulfoxide (DMSO-$d_6$), deuterated chloroform (CDCl$_3$), deuterated methanol (CD$_3$OD), and the internal standard was tetramethylsilane (TMS).

The determination of MS is performed by FINNIGAN LCQAd (ESI) mass spectrometer (manufacturer: Thermo, model: Finnigan LCQ advantage MAX).

HPLC was determined by using Agilent 1200DAD high pressure liquid chromatography (Sunfire C18 150×4.6 mm column) and Waters 2695-2996 high pressure liquid chromatography (Gimini C18 150×4.6 mm column).

Ion Chromatography (HPIC): apparatus: Dionexis-5000+ Ion chromatograph; separation column: IonPac AS11-HC, detection mode: conductance; rinsing solution: NaOH 0.03M; flow rate: 1.5 mL/min

Embodiment 1: Preparation of the Acetate of the Compound Represented by Formula (I)

The compound represented by formula (I) (71 mg, 0.1 mmol) and isopropanol (0.25 mL) were added into a reaction flask, heated to 50° C., stirred until dissolved completely, acetic acid (6 mg, 0.1 mmol) was added dropwise at 50° C., followed by isopropyl ether (0.25 mL), then stirred for 2 hours at 50° C., naturally cooled to room temperature, stirred for 16 hours, the reaction mixture was then filtered, and the filter cake was dried under vacuum to obtain the title product (30 mg, yield 39%).

The $^1$H-NMR of the obtained product was shown below, nuclear magnetic data show that the molar ratio of the main component to acetic acid in the salt is 1:1.

$^1$H-NMR (400 MHz, CD$_3$OD) d 7.37-7.11 (m, 10H), 4.88-4.80 (m, 1H), 4.61 (dd, 1H), 4.40 (dd, 1H), 3.86 (brs., 1H), 3.83-3.58 (m, 3H), 3.24-3.03 (m, 3H), 2.96-2.72 (m, 4H), 2.61 (dd, 1H), 2.52 (dd, 1H), 2.19 (brs., 2H), 1.90 (s, 3H), 1.83-1.53 (m, 9H), 1.44 (d, 2H), 1.19 (d, 3H), 1.01-0.87 (m, 6H).

Embodiment 2: Preparation of the Acetate of the Compound Represented by Formula (I)

The compound represented by the formula (I) (300 mg, 0.424 mmol) was added into dichloromethane (3 mL), stirred and dissolved, a prefabricated solution of acetic acid (26.7 mg, 0.445 mmol) dissolved in 0.5 mL dichloromethane was added, the mixture was then heated to 50° C., stirred for 2 hours in a slightly boiling state, then isopropyl ether (3 mL) was added, stirred for 2 hours at room temperature, the reaction mixture was filtered, and the filter cake was rinsed with isopropyl ether (5 ml*2), drained and dried under vacuum to obtain the title product (300 mg, yield 92%).

The $^1$H-NMR of the obtained product was shown below, nuclear magnetic data show that the molar ratio of the main component to acetic acid in the salt is 1:1.

$^1$H-NMR (400 MHz, CD$_3$OD) δ 7.40-7.12 (m, 10H), 4.88-4.80 (m, 1H), 4.61 (dd, 1H), 4.39 (dd, 1H), 3.97-3.69 (m, 4H), 3.23-3.06 (m, 3H), 2.98-2.73 (m, 4H), 2.61 (dd, 1H), 2.53 (dd, 1H), 2.20 (d, 2H), 1.91 (s, 3H), 1.87-1.74 (m, 2H), 1.74-1.51 (m, 7H), 1.44 (d, 2H), 1.19 (d, 3H), 1.01-0.87 (m, 6H).

Embodiment 3 Preparation of the Acetate of the Compound Represented by Formula (I)

The compound represented by formula (I) (500 mg, 0.042 mmol) and dichloromethane (5 mL) were added into a reaction flask, stirred and dissolved completely, then acetic acid (44.4 mg, 0.741 mmol) was added dropwise, the reaction mixture was heated to 40° C. and the mixture was stirred for 2 hours, then diisopropyl ether (5 mL) was added, slowly cooled to room temperature and continued stirring for 1 hour, the reaction mixture was then filtered, and the filter cake was dried under vacuum to obtain the title product (500 mg, yield: 92%).

The $^1$H-NMR of the obtained product was shown below, nuclear magnetic data show that the molar ratio of the main component to acetic acid in the salt is 1:1.

$^1$H-NMR (400 MHz, CD$_3$OD) δ 7.34-7.05 (m, 10H), 4.83 (dd, 1H), 4.61 (dd, 1H), 4.40 (dd, 1H), 3.93-3.64 (m, 4H), 3.24-3.04 (m, 3H), 2.97-2.76 (m, 4H), 2.68-2.47 (m, 2H), 2.30-2.07 (m, 2H), 1.91 (s, 3H), 1.84-1.55 (m, 9H), 1.44 (d, 2H), 1.19 (d, 3H), 1.06-0.79 (m, 6H).

Embodiment 4 Preparation of the Acetate of the Compound Represented by Formula (I)

The compound represented by formula (I) (300 mg, 0.42 mmol) and dichloromethane (3 mL) were added into a reaction flask, stirred and dissolved completely, a prefabricated solution of acetic acid (76.3 mg, 1.27 mmol) in dichloromethane (0.5 mL) was then added dropwise, the temperature was raised to 50° C. and the mixture was stirred for 2 hours, isopropyl ether (3 mL) was then added, then the temperature was slowly lowered to room temperature and the mixture was stirred for 72 hours at room temperature, the reaction mixture was filtered, and the filter cake was washed with isopropyl ether (5 ml×2), and dried under vacuum to obtain the title product (300 mg, yield 92%).

The of the obtained product is shown below, nuclear magnetic data show that the molar ratio of the main component to acetic acid in the salt is 1:2.

$^1$H-NMR (400 MHz, CD$_3$OD) δ 7.39-7.13 (m, 10H), 4.83 (m, 1H), 4.61 (dd, 1H), 4.39 (dd, 1H), 3.94-3.65 (m, 4H), 3.27-3.12 (m, 3H), 2.95-2.79 (m, 4H), 2.70-2.52 (m, 2H), 2.20 (dd, 2H), 1.93 (s, 6H), 1.84-1.55 (m, 9H), 1.51-1.40 (d, 2H), 1.20 (d, 3H), 1.01-0.87 (m, 6H).

Embodiment 5 Preparation of the Acetate of the Compound Represented by Formula (I)

SepHadex g25 (10 g) was immersed in 20% ethanol aqueous solution for 30 minutes, then filled into the column (diameter:height=1:3, the rest was filled with sea sand), the compound represented by formula (I) (2 g, crude product) and water (2 mL) were added into the reaction flask, aqueous ammonia was added dropwise until pH of the solution was about 7, the sample was load with wet process, rinsed with pure water, collection was conducted at 214 nm and 210 nm peaks, the collected solution was directly lyophilized, and the residue was purified by high performance liquid chromatography (column WATERS 2767 Xbridge 30×150 mm, 5 μm; mobile phase (A: water (0.1% acetic acid), B: water (10 mmol/L ammonium acetate), C: acetonitrile) to obtain the title product (500 mg).

The results of ion chromatography (HPIC) detection of the obtained product showed that the acetate ion content was 13.52%, indicating that the molar ratio of main component to acetic acid in the salt was 1:2.

Embodiment 6 Preparation of the Hydrochloride of the Compound Represented by Formula (I)

The crude compound (2 g, 1.88 mmol) represented by formula (I) was dissolved in hydrochloric acid (16 mL, 4 M), stirred to react for 2 hours, concentrated under reduced pressure to obtain about 2 g crude product, and the crude product was purified by high performance liquid chromatography (chromatographic column: Sharpsil-H 20250 mm; 5 μm; C18; mobile phase (A: water (0.05% HCl), B: acetonitrile)) to obtain the title product (80 mg, yield 70%).

Ion chromatography (HPIC) detection results of the obtained product show that the chloride ion content was 9.73%, indicating that the molar ratio of the main component in the salt to hydrochloric acid was 1:2.

Embodiment 7 Preparation of the Hydrochloride of the Compound Represented by Formula (I)

The compound represented by the formula (I) (100 mg, 0.141 mmol) was dissolved in ethanol (2 mL), a solution of hydrogen chloride in isopropyl alcohol (0.176 ml, 4M) was added dropwise, the mixture was stirred at room temperature for 16 hours without solid precipitation, diisopropyl ether (2 mL) was added, the resultant was stirred for 4 hours, the reaction mixture was filtered, and the filter cake was washed with diisopropyl ether (1 mL), the filter cake was collected, and dried under vacuum to obtain the title product (80 mg, yield 70%).

Ion chromatography (HPIC) detection results of the obtained product show that the chloride ion content was 12.57%, indicating that the molar ratio of the main component in the salt to hydrochloric acid was 1:3.

Embodiment 8 Preparation of the Hydrochloride of the Compound Represented by Formula (I)

The compound represented by the formula (I) (350 mg, 0.494 mmol) was dissolved in isopropanol (5 mL), stirred and fully dissolved, a solution of hydrogen chloride in isopropanol (0.494 ml, 4M) was added dropwise, solid was precipitated, the mixture was stirred for 5 minutes and then completely dissolved, further stirred at room temperature for 16 hours, no solid was precipitated, diisopropyl ether (2 mL) was added, the resultant was stirred at room temperature for 6 hours, reaction mixture was filtered, the filter cake was collected, and dried under vacuum to obtain the title product (250 mg, yield 62%).

Ion chromatography (HPIC) detection results of the obtained product show that the chloride ion content was 12.38%, indicating that the molar ratio of the main component in the salt to hydrochloric acid was 1:3.

Embodiment 9 Preparation of the Hydrochloride of the Compound Represented by Formula (I)

The crude compound represented by formula (I) (4.08 g, crude product) was added to hydrochloric acid (40 mL, 4M) at 0° C., the mixture was stirred at room temperature for 2 hours, concentrated under reduced pressure, and the resulting residue was purified by preparative chromatography to obtain the title product (710 mg, yield 17%).

Ion chromatography (HPIC) detection results of the obtained product show that the chloride ion content was 12.38%, indicating that the molar ratio of the main component in the salt to hydrochloric acid was 1:3.

Embodiment 10 Preparation of the Citrate of the Compound Represented by Formula (I)

The compound represented by the formula (I) (71 mg, 0.1 mmol) was dissolved in isopropanol (0.3 mL), heated to 60° C., a solution of citric acid monohydrate (22 mg, 0.105 mmol) in isopropanol (0.8 mL) was added, the mixture was stirred at 60° C. for 2 hours, cooled to room temperature and stirred for 16 hours, the reaction mixture was filtered, and the filter cake was rinsed with isopropanol (0.6 mL), the filter cake was collected, and dried under vacuum to obtain the title product (60 mg, yield 78%).

The $^1$H-NMR of the obtained product was shown below. Nuclear magnetic data showed that the molar ratio of the main component to the citric acid in the salt was 1:1.

$^1$H-NMR (400 MHz, CD$_3$OD) δ 7.40-7.11 (m, 10H), 4.86-4.79 (m, 1H), 4.58 (m, 1H), 4.43-4.29 (m, 1H), 3.96-3.81 (m, 3H), 3.76 (d, 2H), 3.69-3.51 (m, 2H), 3.22-3.06 (m, 2H), 3.05-2.90 (m, 4H), 2.79 (dd, 2H), 2.70 (s, 2H), 2.33-2.03 (m, 2H), 1.92-1.65 (m, 7H), 1.65-1.49 (m, 2H), 1.42 (brs., 2H), 1.34-1.25 (m, 3H), 1.02-0.84 (m, 6H).

Embodiment 11 Preparation of the Citrate of the Compound Represented by Formula (I)

The compound represented by the formula (I) (500 mg, 0.706 mmol) was dissolved in isopropanol (10 mL), the mixture was stirred and dissolved, heated to 40° C., and a prefabricated solution of citric acid monohydrate (156 mg, 0.741 mmol) in isopropanol (10 mL) was added dropwise, white solid suspending appeared, the mixture was stirred at 40° C. for 2 hours, cooled in an ice bath and stirred for 0.5 hours. The reaction mixture was filtered, the filter cake was rinsed with isopropyl alcohol, then the filter cake was collected and dried under vacuum to obtain the title product (600 mg, yield 94%).

The $^1$H-NMR of the obtained product was shown below. Nuclear magnetic data show that the molar ratio of the main component to citric acid in the salt was 1:1.

$^1$H-NMR (400 MHz, CD$_3$OD) δ 7.48-7.29 (m, 2H), 7.29-7.04 (m, 8H), 4.87-4.81 (m, 1H), 4.56 (dd, 1H), 4.35 (dt, 1H), 3.98-3.75 (m, 4H), 3.75-3.57 (m, 2H), 3.57-3.50 (m, 2H), 3.21-3.14 (m, 1H), 3.13-2.89 (m, 5H), 2.79 (dd, 2H), 2.69 (dd, 2H), 2.30-2.01 (m, 2H), 1.88-1.61 (m, 8H), 1.61-1.49 (m, 1H), 1.49-1.33 (m, 2H), 1.33-1.24 (m, 3H), 1.06-0.76 (m, 6H).

Embodiment 12 Preparation of the Citrate of the Compound Represented by Formula (I)

The compound represented by the formula (I) (300 mg, 0.424 mmol) was dissolved in isopropanol (4 mL), a solution of citric acid monohydrate (187 mg, 0.89 mmol) in isopropanol solution (4 mL) was added at 80° C., dissolved at 80° C., the mixture was stirred for 2 hours, further stirred at room temperature for 72 hours, the solid was filtered out, washed with isopropanol (5 ml×3), and the filter cake was collected, then dried under vacuum to obtain the title product (300 mg, yield 77%).

The $^1$H-NMR of the obtained product was shown below. Nuclear magnetic data show that the molar ratio of the main component to citric acid in the salt was 1:2.

$^1$H-NMR (400 MHz, CD$_3$OD) d 7.43-7.20 (m, 9H), 7.15 (t, 1H), 4.85 (d, 1H), 4.58 (dd, 1H), 4.41-4.26 (m, 1H), 3.92-3.78 (m, 4H), 3.70-3.55 (m, 3H), 3.27-3.00 (m, 4H), 2.99-2.86 (m, 2H), 2.82 (dd, 4H), 2.72 (dd, 4H), 2.32-2.08 (m, 2H), 1.88-1.62 (m, 8H), 1.62-1.48 (m, 2H), 1.48-1.37 (m, 2H), 1.33-1.25 (m, 3H), 1.02-0.88 (m, 6H).

Embodiment 13 Preparation of the Citrate of the Compound Represented by Formula (I)

The compound represented by the formula (I) (300 mg, 0.423 mmol) was dissolved in isopropanol (5 mL), citric acid monohydrate (356.2 mg, 1.69 mmol) was added, and the temperature was raised to 60° C. and the mixture was stirred for 2 hours. The reaction mixture was slowly cooled to room temperature, filtered, the filter cake was collected, and dried under vacuum to obtain the title product (260 mg, yield 66%).

$^1$H-NMR of the obtained product was shown below. Nuclear magnetic data show that the molar ratio of the main component to citric acid in the salt was 1:3.

$^1$H-NMR (400 MHz, CD$_3$OD) δ 7.39-7.32 (m, 2H), 7.32-7.19 (m, 7H), 7.15 (t, 1H), 4.89-4.84 (m, 1H), 4.75-4.57 (m, 1H), 4.40-4.30 (m, 1H), 3.98-3.78 (m, 5H), 3.76-

3.58 (m, 2H), 3.25-3.00 (m, 4H), 2.98-2.88 (m, 3H), 2.85 (dd, 5H), 2.77 (s, 3H), 2.73 (s, 3H), 2.32-2.06 (m, 2H), 1.87-1.65 (m, 7H), 1.65-1.47 (m, 2H), 1.43 (brs., 2H), 1.35-1.26 (m, 3H), 1.01-0.81 (m, 6H).

Embodiment 14 Preparation of the Phosphate of the Compound Represented by Formula (I)

The compound represented by the formula (I) (308 mg, 0.436 mmol) was dissolved in isopropanol (5 mL), phosphoric acid (200 mg, 1.73 mmol, purity 85%) was added, the temperature was raised to 60° C., the reaction mixture was stirred for 2 hours, the temperature was slowly lowered to room temperature, and the stirring was carried out for further 16 hours. The reaction mixture was filtered, the filter cake was collected, and dried under vacuum to obtain the title product (520 mg, yield 51.9%).

Ion chromatography (HPIC) detection results of the obtained product show that the phosphate ion content was 31.43%, indicating that the molar ratio of the main component to the phosphoric acid in the salt was 1:3.

Embodiment 15 Preparation of the Phosphate of the Compound Represented by Formula (I)

The compound represented by the formula (I) (500 mg, 0.706 mmol) was dissolved in isopropyl alcohol (40 mL), the temperature was raised to 40° C., a prefabricated solution of phosphoric acid (369 mg, 3.2 mmol, purity 85%) in isopropyl alcohol (10 mL) was added, and the mixture was stirred at 40° C. for 2 hours and 0° C. for 30 minutes. The reaction mixture was filtered, the filter cake was rinsed with isopropyl alcohol (1 ml×3), then the filter cake was collected and dried under vacuum to obtain the title product (660 mg, yield 90%).

Ion chromatography (HPIC) detection results of the obtained product show that the phosphate ion content was 29.08%, indicating that the molar ratio of the main component to phosphoric acid in the salt was 1:3.

Embodiment 16 Preparation of the Benzoate of the Compound Represented by Formula (I)

The compound represented by the formula (I) (55 mg, 0.077 mmol) was dissolved in isopropanol (1 mL), the mixture was heated to 50° C. and stirred until the completely dissolution, a prefabricated solution of benzoic acid (38 mg, 0.31 mmol) in isopropanol (0.3 mL) was added, the mixture was stirred at 50° C. for 2 hours, slowly cooled to room temperature and continued to stir for 16 hours, the reaction mixture was filtered, the filter cake was collected, and dried under vacuum to obtain the title product (35 mg, yield 54%).

The $^1$H-NMR of the obtained product was shown below. Nuclear magnetic data show that the molar ratio of main component to benzoic acid in the salt was 1:2.

$^1$H-NMR (400 MHz, CD$_3$OD) δ 8.21-7.96 (m, 10H), 7.44-7.21 (m, 10H), 4.84 (d, 1H), 4.69-4.57 (m, 1H), 4.38 (s., 1H), 4.00-3.83 (m, 3H), 3.77 (brs, 2H), 3.31-3.24 (m, 3H), 3.20 (s, 1H), 2.97-2.81 (m, 4H), 2.76-2.60 (m., 2H), 1.83-1.53 (m, 9H), 1.43 (brs, 2H), 1.28-1.18 (m, 3H), 0.95 (d, 3H), 0.91 (d, 3H).

Embodiment 17 Preparation of the Fumarate of the Compound Represented by Formula (I)

The compound represented by formula (I) (50 mg, 0.0706 mmol) was dissolved in isopropanol (0.5 mL), then fumaric acid (33 mg, 0.28 mmol) was added, the temperature was raised to 60° C., and the mixture was stirred for 2 hours, cooled to room temperature, filtered, the filter cake was collected, and dried under vacuum to obtain the title product (26 mg, yield 44.6%).

The $^1$H-NMR of the obtained product was shown below. Nuclear magnetic data show that the molar ratio of main component to fumaric acid in the salt was 1:2.

$^1$H-NMR (400 MHz, CD$_3$OD) δ 7.41-7.31 (m, 2H), 7.31-7.20 (m, 7H), 7.20-7.10 (m, 1H), 6.69 (s, 4H), 4.84 (dd, 1H), 4.73-4.60 (m, 1H), 4.37 (dd, 1H), 3.96-3.78 (m, 3H), 3.78-3.63 (m, 2H), 3.60-3.51 (m, 1H), 3.26-3.15 (m, 1H), 3.13-2.96 (m, 3H), 2.96-2.79 (m, 3H), 2.31-2.08 (m, 2H), 1.83-1.54 (m, 8H), 1.49-1.38 (m, 2H), 1.33-1.26 (m, 3H), 1.00-0.82 (m, 6H).

Embodiment 18 Experiment on Influencing Factors of Crystal Form of the Present Invention Samples of the compound represented by formula (I) and acetate, hydrochloride, citrate and phosphate of the compound represented by formula (I) were respectively placed open and evenly spread, so that the stability of the samples were investigated under the conditions of room temperature, heating (40° C., 60° C.), illumination (4500Lux) and high humidity (RH75% and RH90%). The sampling period is 20 days.

Experimental Results

TABLE 1

Experimental results of influencing factors on free state and salt of the compounds represented by Formula (I)

| Category | | Embodiment 2 | Embodiment 4 | Embodiment 6 | Embodiment 9 | Embodiment 12 | Embodiment 13 | Embodiment 14 | Embodiment 15 | Embodiment 20 |
|---|---|---|---|---|---|---|---|---|---|---|
| Sample (acid/base ratio) | | Acetate (1:1) | Acetate (1:2) | Hydrochloride (1:2) | Hydrochloride (1:3) | Citrate (1:2) | Citrate (1:3) | Phosphate (1:3) | Phosphate (1:3) | Free state |
| Condition | Time (days) | Purity % | Purity % | Purity % | Purity % | Purity % | Purity % | Purity % | Purity % | Purity % |
| 4500 Lux | 0 | 97.65 | 97.70 | 99.32 | 96.50 | 97.04 | 97.39 | 99.19 | 96.32 | 99.68 |
|  | 5 | 96.99 | 95.83 | 97.13 | 95.57 | 96.65 | 97.29 | 99.15 | 96.07 | 97.76 |
|  | 10 | 96.68 | 94.91 | 95.32 | 94.27 | 96.63 | 97.28 | 99.12 | 95.62 | 97.72 |
|  | 20 | 96.72 | 92.17 | 92.39 | 94.24 | 96.77 | 97.28 | 99.12 | 95.76 | 97.15 |
| 25° C. | 5 | 97.64 | 97.56 | 99.27 | / | 96.93 | / | / | / | / |
|  | 10 | 97.64 | 97.44 | 99.27 | / | 96.80 | / | / | / | / |
|  | 20 | 97.63 | 97.28 | 99.30 | / | 96.97 | / | / | / | / |

TABLE 1-continued

Experimental results of influencing factors on free state
and salt of the compounds represented by Formula (I)

| Category | | Embodiment 2 | Embodiment 4 | Embodiment 6 | Embodiment 9 | Embodiment 12 | Embodiment 13 | Embodiment 14 | Embodiment 15 | Embodiment 20 |
|---|---|---|---|---|---|---|---|---|---|---|
| 40° C. | 5 | 96.23 | 86.31 | 99.03 | 96.54 | 96.46 | 97.10 | 99.18 | 96.12 | 97.60 |
|  | 10 | 96.30 | 81.09 | 99.03 | 96.42 | 96.49 | 97.00 | 99.10 | 96.17 | 95.43 |
|  | 20 | 95.70 | 66.14 | 99.06 | 96.41 | 96.50 | 97.00 | 99.09 | 96.19 | 90.85 |
| 60° C. | 5 | 96.11 | 79.36 | 98.99 | 96.42 | 92.99 | 91.27 | 99.19 | 95.89 | 94.11 |
|  | 10 | 95.7. | 71.68 | 98.63 | 96.43 | 90.97 | 87.97 | 99.08 | 95.66 | 89.97 |
|  | 20 | 94.94 | 56.02 | 98.59 | 96.41 | 84.35 | 92.88 | 99.02 | 95.82 | 87.43 |
| RH 75% | 5 | / | / | / | 96.55 | / | 97.39 | 99.15 | / | 99.59 |
|  | 10 | / | / | / | 96.43 | / | 97.35 | 99.14 | / | 99.51 |
|  | 20 | / | / | / | 96.42 | / | 97.34 | 99.15 | / | 99.50 |
| RH 90% | 5 | / | / | / | 96.29 | / | 97.31 | 99.19 | / | 99.60 |
|  | 10 | / | / | / | 96.21 | / | 97.30 | 99.15 | / | 99.58 |
|  | 20 | / | / | / | 96.17 | / | 97.30 | 99.14 | / | 99.55 |

Note:
The symbol "/" indicates that it has not been determined.

Experimental Conclusion

The experimental results of the influencing factors showed that:

the free state degraded greatly under the conditions of illumination and high temperature over 20 days, and high temperature has great influence on the stability of the free state.

Acetate (1:1 or 1:2) degraded varying degrees under illumination, 40° C., 60° C. Acetate (1:2) had poor stability at high temperature. After the 20-day experiment was completed, the results of ion chromatography under high temperature showed that the acetate (radical) content was greatly reduced.

The hydrochloride (1:2) slightly degraded under the condition of illumination and high temperature; the hydrochloride (1:3) slightly degraded under illumination condition and was stable under other conditions.

Citrate (1:2 or 1:3) degraded greatly at the high temperature of 60° C.

Phosphate (1:3) was relatively stable or slightly degraded under illumination and high temperature conditions.

It is suggested that all salt samples should be stored in shade, sealed condition and away from illumination.

Embodiment 19 Long-Term Accelerated Stability Experiment of Different Salt Types of the Compound Represented by Formula (I) of the Present Invention Samples of acetate, hydrochloride, citrate and phosphate of the compound represented by formula (I) were subjected to a long-term accelerated stability investigation for 6 months under dark and sealed conditions (the inner package is a medicinal low-density polyethylene composite film and the outer package is aluminum foil), humidity (60% RH), temperature (4° C., 25° C.) and with/without nitrogen protection.

Experimental Results

TABLE 2

Long-term accelerated stability test results of salts of
the compound represented by formula (I)

| Sample | Placement condition | Aspect Initial | Purity % Initial | Aspect 1 month | Purity % 1 month | Aspect 3 months | Purity % 3 months | Aspect 6 months | Purity % 6 months |
|---|---|---|---|---|---|---|---|---|---|
| Embodiment 3 Acetate (1:1) | 4° C. | White solid | 99.59 | White solid | 99.59 | White solid | 99.58 | White solid | 99.60 |
|  | 25° C., 60% Rh | White solid | 99.59 | White solid | 99.62 | White solid | 99.61 | White solid | 99.57 |
|  | 25° C., 60% RH nitrogen protection | White solid | 99.59 | White solid | 99.58 | White solid | 99.51 | White solid | 99.54 |
| Embodiment 9 hydrochloride (1:1) | 4° C. | White solid | 99.54 | White solid | 99.51 | White solid | 99.51 | White solid | 98.57 |
|  | 25° C., 60% Rh | White solid | 99.54 | White solid | 99.46 | White solid | 99.51 | White solid | 99.51 |
|  | 25° C., 60% RH nitrogen protection | White solid | 99.54 | White solid | 99.52 | White solid | 99.50 | White solid | 98.54 |

TABLE 2-continued

Long-term accelerated stability test results of salts of the compound represented by formula (I)

| Sample | Placement condition | Aspect Initial | Purity % Initial | Aspect 1 month | Purity % 1 month | Aspect 3 months | Purity % 3 months | Aspect 6 months | Purity % 6 months |
|---|---|---|---|---|---|---|---|---|---|
| Embodiment 11 citrate (1:1) | 4° C. | White solid | 99.50 | White solid | 99.49 | White solid | 99.56 | White solid | 99.57 |
|  | 25° C., 60% Rh | White solid | 99.50 | White solid | 99.50 | White solid | 99.52 | White solid | 99.5 |
|  | 25° C., 60% RH nitrogen protection | White solid | 99.50 | White solid | 99.50 | White solid | 99.51 | White solid | 99.51 |
| Embodiment 15 Phosphate (1:3) | 4° C. | White solid | 99.64 | White solid | 99.63 | White solid | 99.62 | White solid | 99.66 |
|  | 25° C., 60% Rh | White solid | 99.64 | White solid | 99.64 | White solid | 99.63 | White solid | 99.64 |
|  | 25° C., 60% RH nitrogen protection | White solid | 99.64 | White solid | 9.65 | White solid | 99.62 | White solid | 99.63 |

Experimental Conclusion

The long-term accelerated stability test results showed that the amorphous samples of acetate (1:1), hydrochloride (1:3), citrate (1:1) and phosphate (1:3) of the compound represented by formula (I) were stable for 6 months under the conditions of 4° C., 25° C., 60% RH, with/without nitrogen protection.

Embodiment 20 the preparation of the compound represented by formula (I) can be referred to the method in WO2017211272 (application No. PCT/CN2017/087328, date of application: Jun. 6, 2017)

4-amino-1-((2R,5R,8R,14R)-2-(4-aminobutyl)-8-benzyl-5-isobutyl-4,7,10-trioxo-14-phenyl-3,6,9,12-tetraazapentadecan-1-acyl)piperidine-4-carboxylic Acid Formula (I)

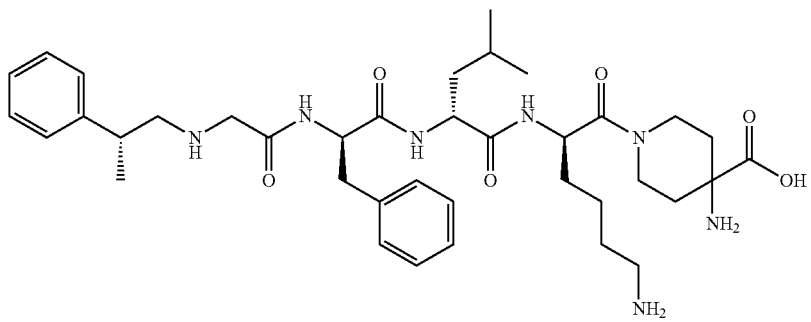

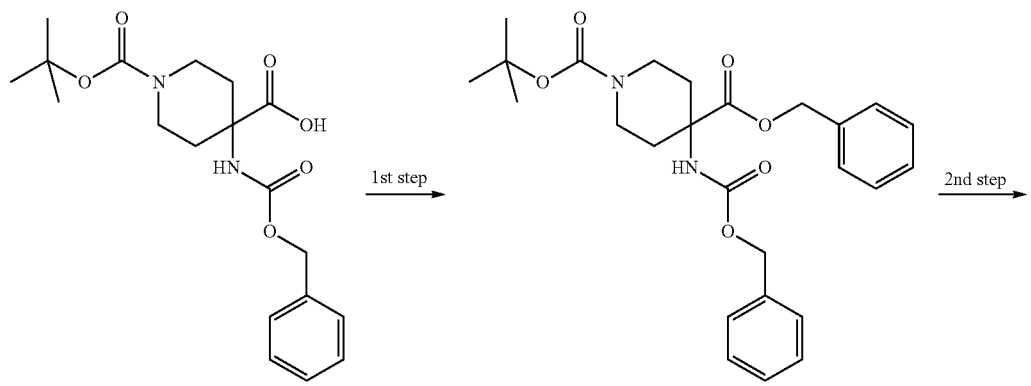

-continued
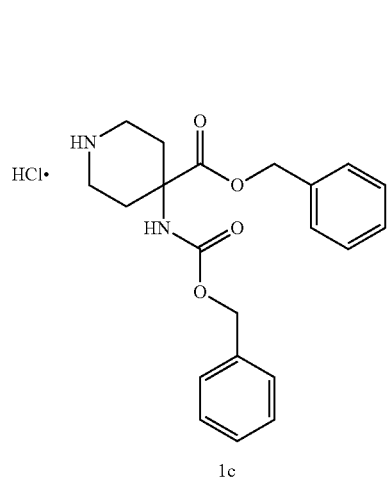
1c
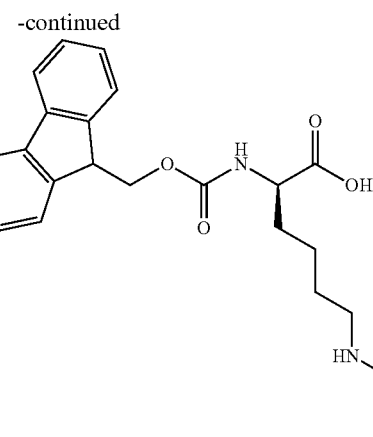
1d
3rd step →
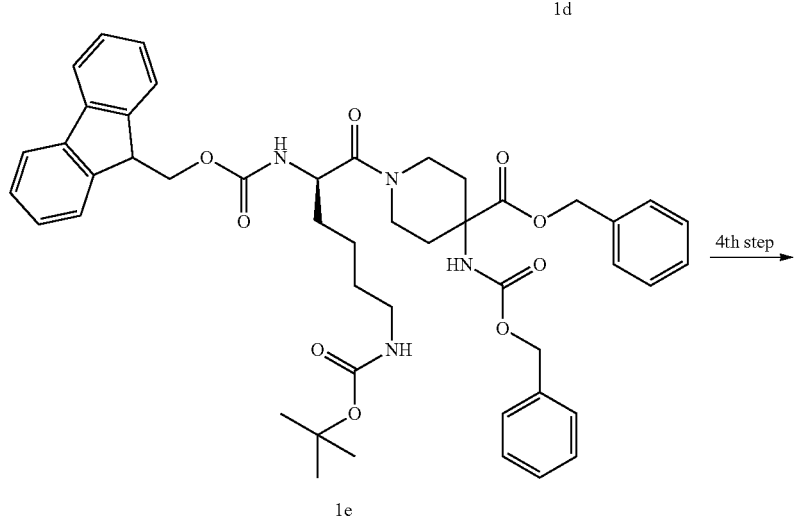
1e
4th step →
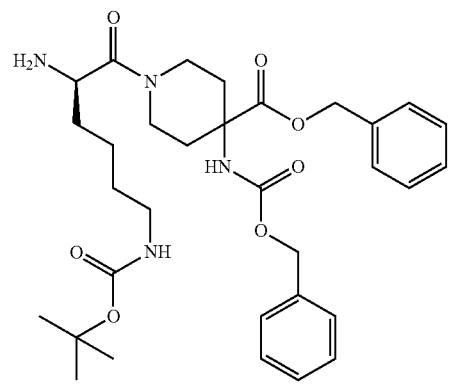
1f
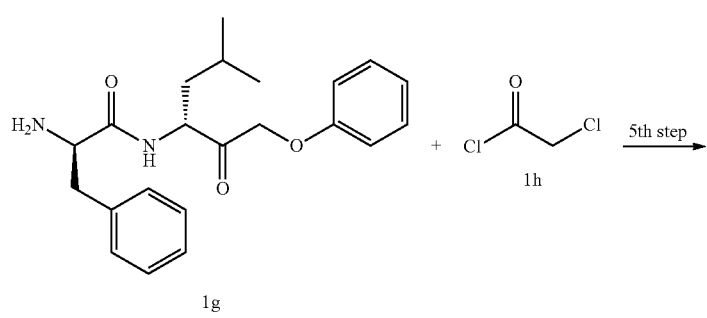
1g
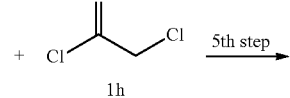
1h
5th step →

-continued
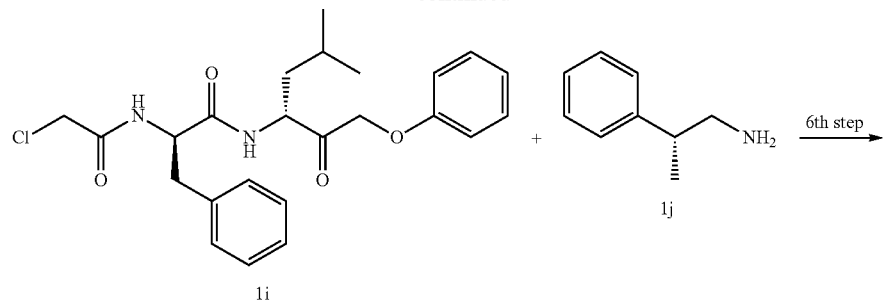
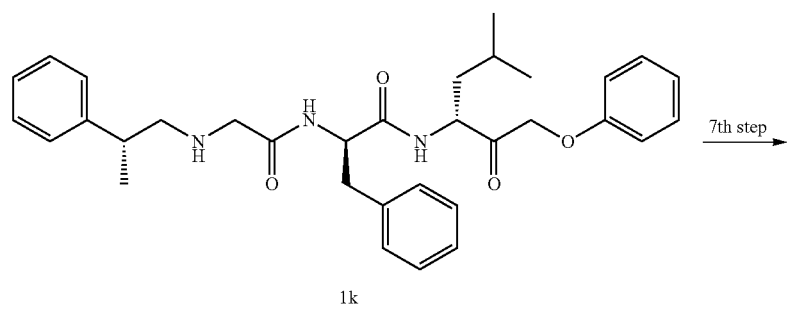
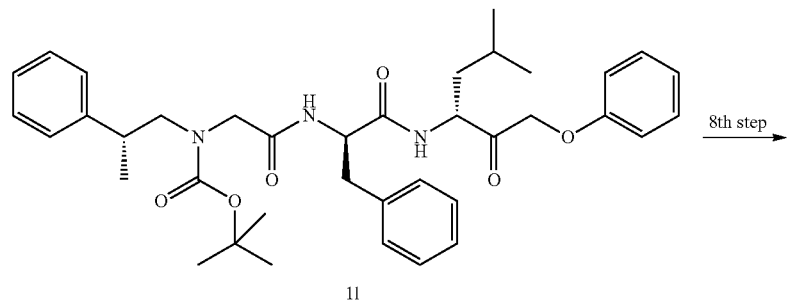
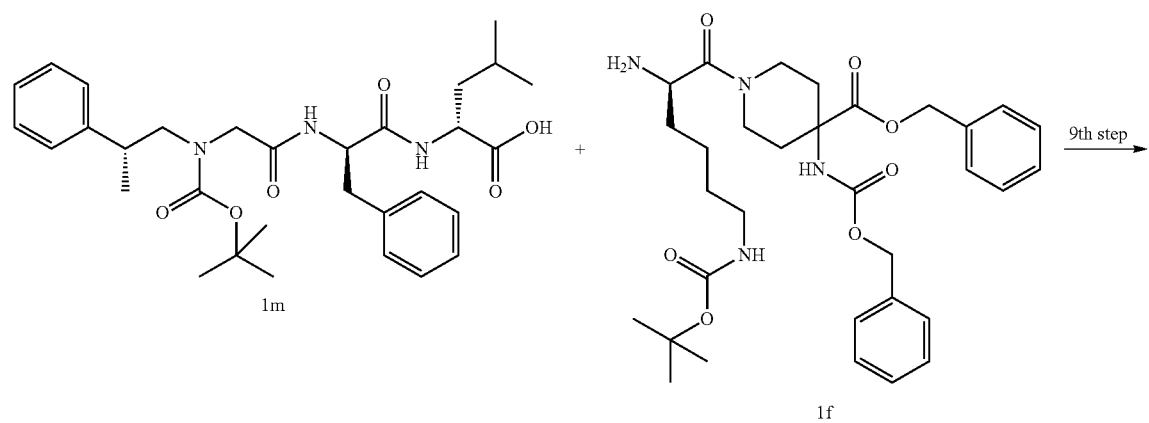

-continued
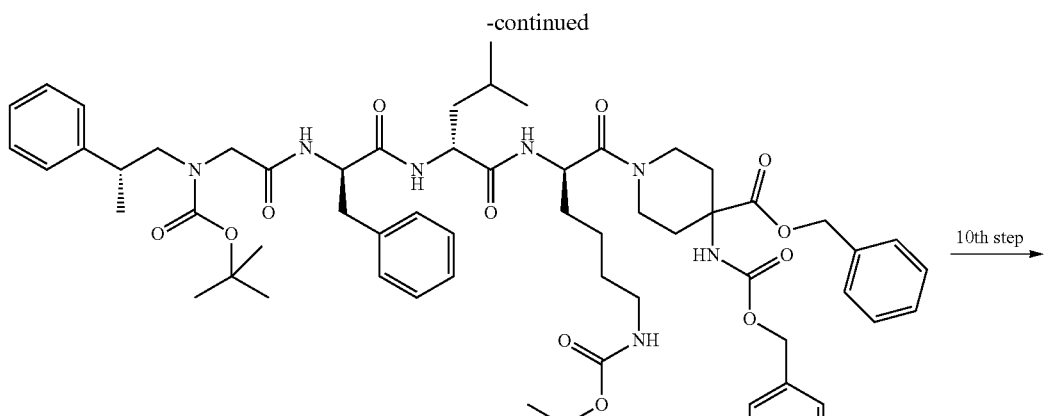
1n
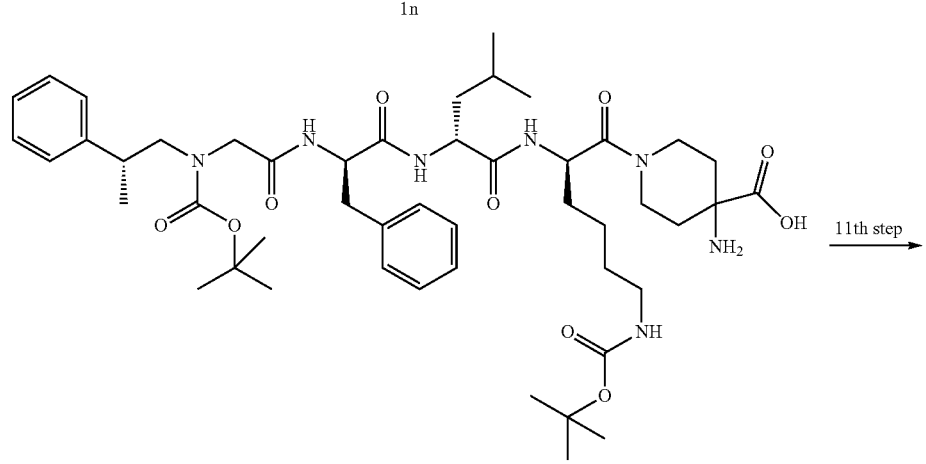
1o
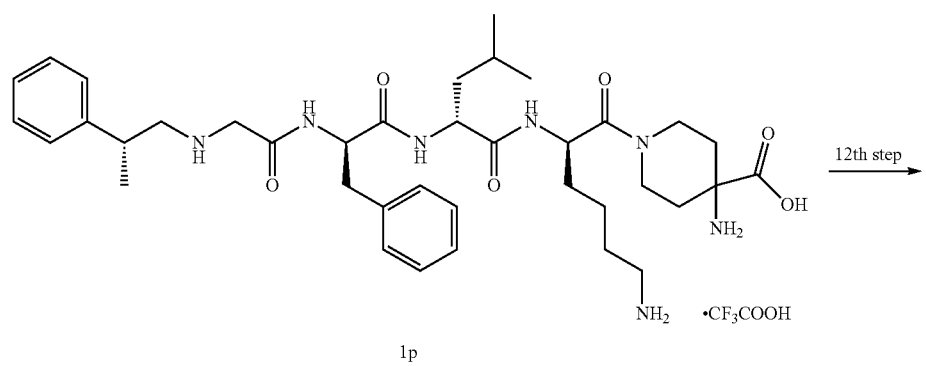
1p
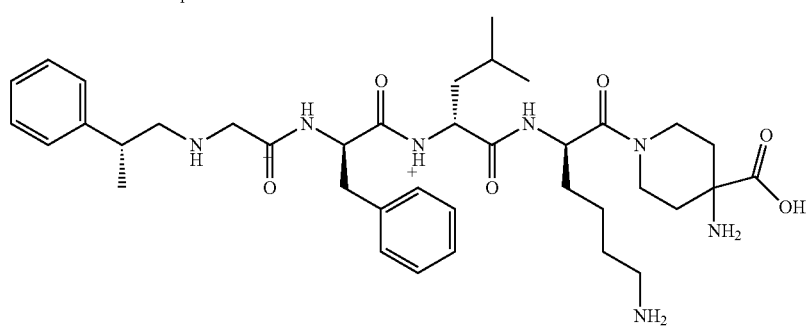
1
formula (I)

Step 1

4-Benzyl 1-tert-butyl 4-(((benzyloxy)carbonyl)amino)piperidine-1,4-dicarboxylic Acid 1b 4-(((benzyloxy)carbonyl)amino)-1-(tert-butoxycarbonyl)piperidine-4-carboxylic acid 1a (1.2 g, 0.0032 mol, prepared by the well-known method "*Bioorganic Medicinal Chemistry Letters,* 2007, 7(9), 2448-2451"), benzyl bromide (0.65 g, 0.0038 mol), cesium carbonate (2.1 g, 0.0064 mol) were dissolved in 20 ml of N,N-dimethyl formamide, and the reaction mixture was stirred at room temperature for 12 hours. The reaction mixture was poured into water, extracted with ethyl acetate (30 ml×3), the organic phases were combined, dried over anhydrous sodium sulfate, filtered, and the filtrate was concentrated under reduced pressure, and the resulting residue was purified by thin layer chromatography (n-hexane and ethyl acetate as eluents) to obtain the title product 1b (800 mg, yield: 53%).

Step 2

Benzyl 4-(((benzyloxy)carbonyl)amino)piperidine-4-carboxylate hydrochloride 1c Compound 1b (800 mg, 1.71 mmol) was dissolved in 2 mL of dichloromethane, then 2 ml of 4 M hydrogen chloride in 1,4-dioxane solution was added, and the reaction mixture was stirred at room temperature for 4 hours. The reaction mixture was concentrated under reduced pressure to obtain the crude title product 1c (800 mg), and the product was directly subjected to the next reaction without purification.

Step 3

Benzyl (R)-1-(2-(((9H-fluorene-9-yl)methoxy)carbonyl)amino)-6-((tert-butoxycarbonyl)amino)hexanoyl)-4-(((benzyloxy)carbonyl)amino)piperidine-4-carboxylate 1e The crude product of 1c (800 mg, 1.97 mmol) and (R)-2-((((9H-fluorene-9-yl)methoxy)carbonyl)amino)-6-((tert-butoxycarbonyl)amino)hexanoic acid 1d (926 mg, 1.97 mmol) was dissolved in 20 ml of N,N-dimethyl formamide by using the well-known method in "*Chem Med Chem,* 2015, 10 (7), 1232-1239", then 2-(7-azobenzotriazole)-N,N,N',N'-tetramethylurea hexafluorophosphate (1.12 g, 3.0 mmol) and N,N-diisopropylethylamine (0.7 mL, 3.94 mmol) were added, and the reaction mixture was stirred at room temperature for 12 hours. The reaction mixture was then poured into a 2N citric acid, extracted with ethyl acetate (30 mL×3), the organic phases were combined, washed with saturated sodium bicarbonate solution, dried over anhydrous sodium sulfate, filtered, and the filtrate was concentrated under reduced pressure to obtain the crude title product 1e (1.6 g). The product was directly subjected to the next reaction without purification.

Step 4

Benzyl (R)-1-(2-amino-6-((tert-butoxycarbonyl)amino)hexanoyl)-4-(((benzyloxy)carbonyl)amino)piperidine-4-carboxylate 1f The crude product of 1e (1.6 g, 0.002 mol) was dissolved in 10 mL of dichloromethane, 10 mL of piperidine was added, and the reaction mixture was stirred at room temperature for 2 hours. After the reaction mixture was concentrated under reduced pressure, the resulting residue was purified by thin layer chromatography (dichloromethane and methanol as eluents) to obtain the title product 1f (900 mg, yield: 77%).

Step 5

Benzyl (R)-2-((R)-2-(2-chloroacetamido)-3-phenylpropanamide)-4-methyl pentanoate 1i Benzyl (R)-2-((R)-2-(2-amino-3-phenylpropanamide)-4-methyl pentanoate 1g (500 mg, 1.36 mmol, prepared by the method disclosed in patent application "US20110212882A1") and triethylamine (275 mg, 2.72 mmol) were dissolved in 10 mL of dichloromethane, then chloroacetyl chloride (230 mg, 2 mmol) was added dropwise, and the reaction mixture was stirred at room temperature for 12 hours. The reaction mixture was poured into water, washed with saturated ammonium chloride solution, the organic phase was dried over sodium sulfate, filtered, and the filtrate was concentrated under reduced pressure to obtain the crude title product 1i (500 mg). The product was directly subjected to the next reaction without purification.

Step 6

Benzyl (R)-4-methyl-2-((R)-3-phenyl-2-(2-(((R)-2-phenylpropyl)amino)acetamido)propionamido) pentanoate 1k The crude product of the compound 1i (500 mg, 1.12 mmol) and (R)-2-phenylpropan-1-amine 1j (228 mg, 1.68 mmol, prepared by the well-known method "*Angewandte chemie, international edition,* 2003, 42 (39), 4793-4795") were dissolved in 10 ml of N,N-dimethyl formamide, then potassium iodide (372 mg, 2.24 mmol) and potassium carbonate (309 mg, 2.24 mmol) were added, and the mixture was heated to 60° C. and stirred for 12 hours. The reaction mixture was cooled to room temperature, water was added, then extracted with dichloromethane (30 mL×3), organic phases were combined, dried over anhydrous sodium sulfate, filtered, and the filtrate was concentrated under reduced pressure to give the crude product of the title compound 1k (600 mg). The product was directly subjected to the next reaction without purification.

Step 7

Benzyl (9R,12R)-9-benzyl-12-isobutyl-2,2-dimethyl-4,7,10-trioxy-5-((R)-2-phenylpropyl)-3-oxa-5,8,11-triaza-13-tridecanoate 1l The crude product of the compound 1k (600 mg, 1.1 mmol) was dissolved in 20 mL of dichloromethane, di-tert-butyl dicarbonate (361 mg, 1.66 mmol) and triethylamine (222 mg, 2.2 mmol) were added, and the reaction mixture was stirred at room temperature for 12 hours. The reaction mixture was concentrated under reduced pressure, and the resulting residue was purified by thin layer chromatography (dichloromethane and methanol as eluents) to obtain the title product 1l (580 mg, yield: 82%).

Step 8

(9R,12R)-9-benzyl-12-isobutyl-2,2-dimethyl-4,7,10-trioxy-5-((R)-2-phenylpropyl)-3-oxa-5,8,11-triaza-13-tridecanoic Acid 1m The compound 1l (580 mg, 0.9 mmol) was dissolved in 10 mL of methanol, then palladium carbon (60 mg, catalytic amount) was added, after the addition, the mixture was ventilated with hydrogen for three times, and the reaction mixture was stirred at room temperature for 12 hours. The reaction mixture was filtered with diatomite, and the filtrate was concentrated under reduced pressure to obtain the crude title product 1m (500 mg). The product was directly subjected to the next reaction without purification.

Step 9

Benzyl 1-((9R,12R,15R)-9-benzyl-15-(4-((tert-butoxycarbonyl)amino)butyl)-12-isobutyl-2,2-dimethyl-4,7,10,13-tetraoxy-5-((R)-2-phenylpropyl)-3-oxa-5,8,11,14-tetraazahexadecyl-16-acyl)-4-(((benzyloxy)carbonyl)amino)piperidine-4-carboxylate 1n The crude product of the compound 1m (365 mg, 0.66 mmol), 1f (393 mg, 0.66 mmol), 2-(7-azobenzotriazole)-N,N,N',N'-tetramethylurea hexafluorophosphate (376 mg, 0.99 mmol) and N,N-diisopropylethylamine (0.16 mL, 0.99 mmol) were dissolved in 10 ml of N,N-dimethyl formamide, and the reaction mixture was stirred at room temperature for 2 hours. Then the reaction mixture was concentrated under reduced pressure, and the resulting residue was purified by thin layer chromatography (dichloromethane and methanol as eluents) to obtain the title product 1n (170 mg, yield: 23%).

Step 10

4-Amino-1-((9R,12R,15R)-9-benzyl-15-(4-((tert-butoxycarbonyl)amino)butyl)-12-isobutyl-2,2-dimethyl-4,7,10,13-tetraoxo-5-((R)-2-phenylpropyl)-3-oxa-5,8,11,14-tetraazacetyl-16-acyl)piperidine-4-carboxylic Acid 1o The compound 1n (80 mg, 0.0706 mmol) was dissolved in 10 mL of methanol, palladium carbon (10 mg, catalytic amount) was added, the mixture was ventilated with hydrogen for three times after the addition, and the reaction mixture was stirred at room temperature for 12 hours. The reaction mixture was filtered with diatomite, and the filtrate was concentrated under reduced pressure to obtain the crude title product 1o (60 mg). The product was directly subjected to the next reaction without purification.

Step 11

4-Amino-1-((2R,5R,8R,14R)-2-(4-aminobutyl)-8-benzyl-5-isobutyl-4,7,10-trioxy-14-phenyl-3,6,9,12-tetraazapentadecyl-1-acyl)piperidine-4-carboxylic acid trifluoroacetate 1p The crude compound of 1o (60 mg, 0.066 mmol) was dissolved in 2 mL of dichloromethane, then 1 ml solution of 4 M hydrogen chloride in 1,4-dioxane was added, and the reaction mixture was stirred at room temperature for 2 hours. The reaction mixture was concentrated under reduced pressure and the residue was purified by high performance liquid chromatography to obtain the title product 1p (30 mg, yield: 55.6%).

MS m/z (ESI): 708.6 [M+1]

Step 12

4-Amino-1-((2R,5R,8R,14R)-2-(4-aminobutyl)-8-benzyl-5-isobutyl-4,7,10-trioxy-14-phenyl-3,6,9,12-tetraazapentadecyl-1-acyl)piperidine-4-carboxylic Acid Formula (I)

The compound 1p (1 g, 0.95 mmol) was dissolved in 10 mL of water, cooled in an ice bath, then aqueous ammonia was added dropwise until pH=7-8, the reaction mixture was stirred for 0.5 hours, concentrated under reduced pressure, and prepared and purified by high performance liquid chromatography to obtain the title product (600 mg, yield: 89%).

MS m/z (ESI): 708.6 [M+1]
$^1$H-NMR (400 MHz, CD$_3$OD) 7.32-7.18 (m, 10H), 4.86-4.84 (m, 1H), 4.61 (dd, 1H), 4.40 (dd, 1H), 3.86 (brs, 1H), 3.83-3.58 (m, 3H), 3.24-3.03 (m, 3H), 2.96-2.72 (m, 4H), 2.61 (dd, 1H), 2.52 (dd, 1H), 2.19 (brs, 2H), 1.83-1.53 (m, 9H), 1.44 (d, 2H), 1.18 (d, 3H), 0.96-0.90 (m, 6H).

Test Example 1

1. Purpose of the Experiment

The purpose of this experiment is to test the agonistic effect of the compound represented by formula (I) on human KOR (h-KOR) receptor, and evaluate the in vitro activity of the compound according to $EC_{50}$ value.

2. Test of h-KOR Activity 2.1 Purpose of the Experiment

The compound of the present invention can activate the h-KOR receptor, thereby reducing the intracellular cAMP level; the second messenger cAMP enters the nucleus and combines with CRE of DNA to initiate the expression of Luciferase downstream, the luciferase reacts with its substrate to emit fluorescence, and the excitation activity of the compound is reflected by the measuring of the fluorescence signal.

2.2 Experimental Methods

The activity of the compound represented by formula (I) activating h-KOR thereby influencing the level of downstream cAMP is tested by the following method.

2.2.1 Experimental Materials and Apparatus

1) Experimental apparatus 1. microplate reader (PE, Vector3)

2) experimental materials

| Reagent | Supply company | No |
|---|---|---|
| HEK293 cell line | Cell Bank of Typical Culture Preservation Committee of Chinese Academy of Sciences | GNHu43 |
| DMSO | Shanghai titanchem | G75927B |
| DMEM high sugar medium | Thermo HyCLone | SH30243018 |
| Fetal bovine serum (FBS) | Gibco | 10099-141 |
| CRE/pGL4.29 | Promega | E8471 |
| KOR-1/pcDNA3.1(+) | GENEWIZ Biotechnology Synthesis Co, Ltd. | |
| ONE-Glo Luciferase Assay System | Promega | E6110 |

2.2.2 Experimental Steps

1) The Preparation of HEK293/KOR/CRE Monoclonal Cell Lines

Human KOR/pcDNA3.1(+) and CRE/pGL4.29 were transferred into HEK293 cell lines by adding G418 and hygromycin to the culture medium, and HEK293/KOR/CRE monoclonal cell lines were screened out from 96-well plate.

2) Experiment on Activating Effects of the Compound Represented by Formula (I) on h-KOR HEK293/h-KOR/CRE monoclonal cell lines were incubated in DMEM/high glucose medium (10% FBS, 1 mg/ml G418, 200m/mL hygromycin, mixed evenly) and passaged every 3 days. On the day of the experiment, the cell suspension was prepared with fresh cell culture medium, the 96-well plate (BD, #356692) was incubated with 20,000 cells/well and the incubation was carried out at 37° C. with 5% carbon dioxide. On the next day, the compound represented by formula (I) was dissolved in pure DMSO at a concentration of 20 mM, and then the first concentration of 200 nM was prepared with DMSO, then the compound was serially diluted 3 fold to 8 concentrations, and 90 μL of DMSO was added to the blank and control wells; then the culture medium was diluted 20 times with DMEM/high glucose (SH30243.01B, Hyclone) containing 10 μM Forskolin. The cell culture plate inoculated on the first day was taken out, then 10 μl diluted drug or control (0.5% DMSO) was added into each well, gently shook and mixed, and placed at 37° C. for 4 hours. In the 96-well plate, 100 μl luciferase detection solution (Promega, # E6110) was added to each well, and the plate was left at room temperature for 5 minutes, the chemiluminescence value was measured by Victor3.0. The $EC_{50}$ value of the compound was calculated by Graphpad Prism software according to the concentration of the compound and the corresponding signal value.

2.3 Test Results

The compound represented by formula (I) is of EC50=1 pM in activating the h-KOR receptor to affect the level of cAMP, and the compound has obvious activating effect on h-KOR receptor.

Pharmacokinetic Evaluation

Test Example 2: Canine Pharmacokinetic Test

1. Summary

Beagle dogs were used as test animals, and LC/MS/MS methods were used to determine the drug concentration in plasma of Beagle dogs at different time points after intravenous administration of the compound represented by formula (I). To study the pharmacokinetic behavior of the compound of the present invention in Beagle dogs and evaluate its pharmacokinetic characteristics.

2. Test Plan 2.1 Test Drugs

Compound represented by formula (I)

2.2 Experimental Animals 3 male beagle dogs provided by Medicilon Pharmaceutical Technology (Shanghai) Co, Ltd in each group.

2.3 Drug Preparation

A proper amount of sample was weighted and 100% normal saline was added for dissolution.

2.4 Administration

Beagle dogs 3, male, for one group; intravenous administration with a volume of 2 ml/kg after fasting for one night.

3. Operation

For the intravenous administration group, 1.0 ml of blood was collected from jugular vein before and 5 mins, 15 mins, 0.5, 1.0, 2.0, 4.0, 8.0, 12.0, 24.0 hrs after administration, then placed in a heparinized test tube, centrifuged at 3500 rpm for 10 mins to separate plasma, and stored at −80° C.

LC/MS/MS method was used to determine the content of compound in Beagle dog plasma after intravenous administration.

4. Pharmacokinetic Parameters of Beagle Dogs

The pharmacokinetic parameters of the compound represented by formula (I) in Beagle dogs were as follows:

| Pharmacokinetic experiment (0.3 mg/kg) | | | | | |
| --- | --- | --- | --- | --- | --- |
| Embodiment No. | Curve area AUC (ng/mL*h) | Half-time $t_{1/2}$(h) | Residence time MRT(h) | Clearance rate CL (ml/min/kg) | Apparent volume of Distribution Vz (ml/kg) |
| 20 | 1975 ± 165 | 1.34 ± 0.04 | 1.43 ± 0.08 | 2.54 ± 0.21 | 296 ± 19 |

Conclusion: The compound has good pharmacokinetic properties in Beagle dogs.

Test Example 3 Experimental Report of the KOR Agonists in Treating Inflammatory Pain Induced by Carrageenan in Rats

1. PURPOSE OF EXPERIMENT

Establishing the rat carrageenan inflammatory pain model and evaluating the therapeutic effect of KOR agonist on inflammatory pain in rats.

2. EXPERIMENTAL METHODS AND MATERIALS 2.1. Laboratory Animals and Feeding Conditions Male Wistar rats for experiment purchased from Shanghai Slack Experimental Animal Co, Ltd. (Shanghai, China, certificate No. 2015000513408, license SOCK (Shanghai) 2012-0002, 150-180 g at the time of purchase, 5 rats/cage, 12/12 hour light/dark cycle adjustment, constant temperature of 23±1° C., humidity of 50-60%, free intake of water. After the animals were purchased, they were reared for more than 7 days to start the experiment.

2.2. Experimental Drugs

Compounds represented by formula (I);

λ-carrageenan: batch number: BCBP8978V, sigma product.

0.9% sodium chloride solution (500 ml: 4.5 g)

1% λ-carrageenan mixed with physiological saline and stirred overnight, forming a jelly suspension.

The drug dosage was calculated on the basis of base.

2.3. Experimental Design and Methods 2.3.1. Animal Grouping:

After reared, rats were divided into the following groups:

| Inflammatory pain model grouping | n | Molding method | Administration mode |
| --- | --- | --- | --- |
| Blank control group | 8 | 0.9% NS (s.c., 0.1 ml/rat, single) | 0.9% NS (i.v single) |
| Model group | 8 | 1% λ-carrageenan (s.c., 0.1 ml/rat, single) | 0.9% NS (i.v single) |

-continued

| Inflammatory pain model grouping | n | Molding method | Administration mode |
|---|---|---|---|
| Compounds represented by formula (I) (0.1 and 0.3 mg/kg) | 8 | 1% λ-carrageenan (s.c., 0.1 ml/rat, single) | Compound of formula (I) (0.1, 0.3 mg/kg i.v single) |

Note: NS: physiological saline for preparing carrageenan solution; i.v.: intravenous injection; s.c.: subcutaneous injection.

2.3.2. Experimental Methods[1]:

The experimental method was improved according to the method in document 1 (Kazunari Nakao et al.). Before the inflammatory pain experiment, rats were randomly divided into the following groups according to body weight: blank control group, model group, 0.1 mg/kg group and 0.3 mg/kg group. There were 8 rats in each group. Inflammatory pain model was established by subcutaneous injection of 1% carrageenan (100 μl) into the foot pad of Wistar rats. After 4 hours, the rats were tested for plantar tenderness to evaluate their mechanical pain threshold, the rats were administrated single caudal vein administration (1 ml/kg) 30 min before the test, and the control group and model group were given the corresponding solvents.

Note: reference 1, CJ-023,423, a Novel, Potent and Selective Prostaglandin KOR Receptor Antagonist with Antihyperalgesic Properties[J]. *The Journal of Pharmacology and Experimental Therapeutics*, 2007, 322(2):686-694.

2.4. Experimental Apparatus

Electronic Von Frey: UGO BASILE, type 38450.

2.5. Data Expression and Statistical Processing

The experimental data were expressed by Mean±standard deviation (S.D.). Statistical comparison was carried out with Excel software T test. The data of the model group and the blank control group were analyzed and compared to see if there was any significant statistical significance. *P<0.05 indicates that there were significant differences between the model groups and the control group, **P<0.01 indicates that there were highly significant differences between the model groups and the control group. # P<0.05 indicates that there were significant differences between the model groups and the administration groups, and ## P<0.01 indicates that there were highly significant difference between the model groups and the administration groups.

3. RESULTS the tenderness threshold of the rats in the blank control group was about 20 g, and that of the model group was 7.6 g, compared with the blank control group, the tenderness threshold of the rats in the model group decreased significantly (p<0.01); compared with the model group, all the drugs can significantly increase the tenderness threshold of inflammatory rats (P<0.01), the tenderness thresholds of 0.1 mg/kg and 0.3 mg/kg were 13.7 g and 23.2 g respectively, and the increase ranges were 79.5% and 204.5% respectively, with obvious dose dependence (FIG. 1).

4. DISCUSSION

λ-Carrageenan was a colloidal substance extracted from aquatic plant carrageenan, which has an allergic stimulation effect. Carrageenan alone in the experiment can induce inflammation and cause pain. In the present experiment, carrageenan inflammatory pain model was established to observe the change of tenderness threshold after KOR agonist was administrated to rats, and to evaluate the analgesic effect of drugs on sub-acute inflammatory pain and its action intensity. In the experiment, the response of rats to tenderness was measured by an Electronic Von Frey, the Electronic Von Frey (e-VF) was originally designed by Ugo Basile to evaluate allergy and touch-induced pain in mice and rats. The device can automatically record the stimulation time and stimulation intensity of animals. The unique triangular prism design makes it very easy to observe the plantar region of the tested animal during the experiment. During the testing process, the equipment can automatically sense the tested animal to retract the tested claw, and manually judge through the foot switch is also possible. The localization is more concentrated, and is more suitable for measuring local pain and neuropathic pain.

5. CONCLUSION

The tested drugs can improve inflammatory pain in rats and is dose dependence.

What is claimed is:

1. A pharmaceutically acceptable salt of the compound 4-amino-1-((2R,5R,8R,14R)-2-(4-aminobutyl)-8-benzyl-5-isobutyl-4,7,10-trioxo-14-phenyl-3,6,9,12-tetraazapentadecan-1-acyl) piperidine-4-carboxylic acid represented by formula (I),

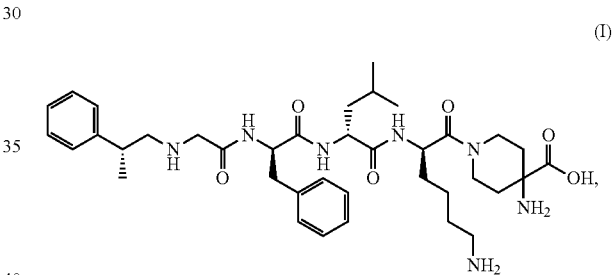

wherein the pharmaceutically acceptable salt is an inorganic salt or an organic salt.

2. The pharmaceutically acceptable salt as defined in claim 1, wherein the molar ratio of the compound represented by the formula (I) to an acid molecule is 1:1 to 1:5.

3. The pharmaceutically acceptable salt as defined in claim 1, wherein,
the molar ratio of the compound represented by the formula (I) to a hydrogen chloride molecule is 1:1, 1:2 or 1:3;
the molar ratio of the compound represented by the formula (I) to a phosphoric acid molecule is 1:3;
the molar ratio of the compound represented by the formula (I) to a citric acid molecule is 1:1, 1:2 or 1:3;
the molar ratio of the compound represented by the formula (I) to a benzoic acid molecule is 1:2; or
the molar ratio of the compound represented by the formula (I) to a fumaric acid molecule is 1:2.

4. The pharmaceutically acceptable salt as defined in claim 1, wherein the pharmaceutically acceptable salt is an acetate, a hydrochloride, a phosphate, a citrate, a benzoate or a fumarate.

5. The pharmaceutically acceptable salt as defined in claim 2, wherein the molar ratio of the compound represented by the formula (I) to the acid molecule is 1:1, 1:2 or 1:3.

6. The pharmaceutically acceptable salt as defined in claim 3, wherein, the molar ratio of the compound represented by the formula (I) to the hydrogen chloride molecule is 1:3; or the molar ratio of the compound represented by formula (I) to the citric acid molecule is 1:1.

7. A pharmaceutical composition comprising the pharmaceutically acceptable salt as defined in claim 1 and optionally a pharmaceutically acceptable carrier, diluent or excipient.

8. A method for preparing the pharmaceutically acceptable salt as defined in claim 3, wherein the method comprises salifying the compound represented by formula (I) with an acid in a salification reaction, wherein the acid comprises hydrogen chloride, phosphoric acid, citric acid, benzoic acid or fumaric acid.

9. The method as defined in claim 8, wherein the salification reaction is carried out in a solvent, and the solvent is an alcohol solvent, a halogenated hydrocarbon solvent, an ether solvent, a nitrile solvent, a mixed solvent of alcohol solvent and ether solvent or a mixed solvent of halogenated hydrocarbon solvent and ether solvent.

10. The method as defined in claim 9, wherein after the completion of the salification reaction step, the method further comprises adding an antisolvent, volatilizing the solvent or cooling is further added, wherein the antisolvent is an ether solvent.

11. The method as defined in claim 9, wherein the alcohol solvent is methanol, ethanol, isopropanol or n-butanol, the ether solvent is diethyl ether, methyl tent-butyl ether, isopropyl ether or dioxane, the nitrile solvent is acetonitrile, and the halogenated hydrocarbon solvent is dichloromethane, the mixed solvent of the alcohol solvent and ether solvent is a mixed solvent of ethanol/isopropyl ether or a mixed solvent of ethanol/isopropanol/isopropyl ether, and the mixed solvent of the halogenated hydrocarbon solvent and the ether solvent is a mixed solvent of dichloromethane/isopropyl ether.

12. The method as defined in claim 10, wherein the ether solvent is diethyl ether, methyl tent-butyl ether, isopropyl ether or dioxane.

13. A method for preparing the pharmaceutically acceptable salt as defined in claim 3, wherein the method adopts a salt conversion method, the salt conversion method comprises converting a trifluoroacetate of the compound represented by formula (I) into an acetate of the compound represented by formula (I) comprising subjecting the trifluoroacetate of the compound represented by formula (I) to high performance liquid chromatography and eluting with water containing acetic acid as an eluent, concentrating and drying to obtain the acetate of the compound represented by formula (I).

14. The method as defined in claim 13, wherein the eluent further comprises ammonium acetate, acetonitrile or ammonium acetate/acetonitrile.

15. The method as defined in claim 13, wherein the volume ratio of acetic acid in the eluent is 0.1%.

16. A method of treating a related disease mediated by κ-opioid receptor agonist comprising administering to an individual in need thereof a pharmaceutical composition of claim 7, wherein the disease comprises pain, inflammation, pruritus, edema, hyponatremia, hypokalemia, intestinal obstruction, cough and glaucoma.

17. The method of claim 16, wherein the disease is pain selected from the group consisting of neuropathic pain, trunk pain, visceral pain, skin pain, arthritic pain, kidney stone pain, uterine spasm, dysmenorrhea, endometriosis, dyspepsia, post-surgical pain, post-medical treatment pain, eye pain, otitis pain, explosive cancer pain and pain associated with GI disorder.

* * * * *